United States Patent
Wang et al.

(10) Patent No.: US 10,210,614 B2
(45) Date of Patent: Feb. 19, 2019

(54) KIND OF LUNG LOBE CONTOUR EXTRACTION METHOD AIMING AT DR RADIOGRAPHY

(71) Applicant: SICHUAN UNIVERSITY, Chengdu, Sichuan (CN)

(72) Inventors: Junfeng Wang, Chengdu (CN); Peng Tang, Chengdu (CN); Yulin Ji, Chengdu (CN); Zongan Liang, Chengdu (CN); Yihua Du, Chengdu (CN)

(73) Assignee: SICHUAN UNIVERSITY, Chengdu (CN)

( * ) Notice: Subject to any disclaimer, the term of this patent is extended or adjusted under 35 U.S.C. 154(b) by 42 days.

(21) Appl. No.: 15/598,686

(22) Filed: May 18, 2017

(65) Prior Publication Data
US 2018/0082423 A1    Mar. 22, 2018

(30) Foreign Application Priority Data
Sep. 20, 2016   (CN) .......................... 2016 1 0834885

(51) Int. Cl.
| | |
|---|---|
| *G06T 7/00* | (2017.01) |
| *G06T 7/13* | (2017.01) |
| *A61B 5/00* | (2006.01) |
| *A61B 6/00* | (2006.01) |
| *G06T 7/73* | (2017.01) |

(52) U.S. Cl.
CPC .......... *G06T 7/0014* (2013.01); *A61B 5/7225* (2013.01); *A61B 6/50* (2013.01); *A61B 6/5211* (2013.01); *A61B 6/5217* (2013.01); *G06T 7/13* (2017.01); *G06T 7/74* (2017.01); *G06T 2207/10116* (2013.01); *G06T 2207/20016* (2013.01); *G06T 2207/20081* (2013.01); *G06T 2207/30061* (2013.01)

(58) Field of Classification Search
None
See application file for complete search history.

(56) References Cited

U.S. PATENT DOCUMENTS

| | | | | |
|---|---|---|---|---|
| 2005/0018890 A1* | 1/2005 | McDonald | ............. | A61B 6/481 |
| | | | | 382/128 |
| 2011/0019886 A1* | 1/2011 | Mizuno | ................ | G06T 7/0014 |
| | | | | 382/128 |
| 2014/0334708 A1* | 11/2014 | Sakata | ................ | A61B 6/5288 |
| | | | | 382/131 |

\* cited by examiner

*Primary Examiner* — Delomia L Gilliard
(74) *Attorney, Agent, or Firm* — Oliff PLC

(57) ABSTRACT

A lung lobe contour extraction method aiming at DR radiography, which includes the steps: Obtain the representative lung lobe contour template through offline training; initialize the extraction system of contour lobe area in the chest DR radiography; According to dimension of DICOM image, conduct three-layer pyramid decomposition on the images; Use Gabor filter bank to rebuild pending images; Convert residual error of the rebuilt image by the Gabor filter into black and white image; Use Zhan-Suen refinement algorithm to refine the black and white image; Call every template of the offline training and use them as the convolution kernel operator, conduct convolution on the contour imagep; Filter the local optimum convolution value with optimum possibility from the convolution results and combine the evaluations; Generate the lung lobe contour shape in accordance with the upper and lower templates of optimum matching and its position.

6 Claims, 3 Drawing Sheets

KIND OF LUNG LOBE CONTOUR EXTRACTION METHOD AIMING AT DR RADIOGRAPHY

FIELD OF TECHNOLOGY

This invention involves the medical informatization field especially involves the lung lobe contour extraction method in the diagnosis assistance of the large-scale screening to the tuberculosis infectious disease.

BACKGROUND TECHNOLOGY

DR is short for Digital Radiography. The chest DR radiography image is the replacement of the traditional chest perspective imaging, whose imaging sharpness is high and the radiation is low. X-ray imaging is the major measures of the medical screening for the pulmonary diseases, which include the pulmonary inflammation, lump, tuberculosis, lung cancer and so on. The chest DR radiography utilizes the image difference for the density difference of the human tissue under X-ray to observe the lesion of the parts with slight difference between the thickness and density. However, the structure of human tissue is complicated. The thoracic cavity and enterocoelia include the key organs of the human body, which include all kinds of visceral organs with high density and low density. Therefore, the images of all organs and tissues overlap with each other, which have quite a large influence on the observation and judgment. So the reading and judgment of the DR radiography have very high requirement on the experience of the doctors and the large scale DR radiography examinations are very hard to be launched in the primary hospitals and medical examination points In the resident medical examination, normally the aim of shooting DR radiography is to conduct the tuberculosis screening. The tuberculosis is caused by the mycobacterium tuberculosis, which is easily spread through spray in the air and even the aerosol. The majority of tuberculosis patients is young adults, which will result in the labor loss for the families and the society. The world health organization indicates that the tuberculosis is the important public health problem all over the world. Every year the tuberculosis kills 140,000 people all over the world. In our country, there are approximate 5,000,000 active pulmonary tuberculosis patients at present and there are approximate 50000 people die of tuberculosis every year. In accordance with the estimation of the world health organization, there are approximate 1,000,000 new patients in our country, for which the annual progressive decrease range is 3%. In 22 countries with high burden of the tuberculosis all over the world, our country ranks only second to India. The tuberculosis is one of the major infectious diseases which are importantly prevented and controlled by our country. The Chinese Center for Disease Control and Prevention indicates that our country is one of 22 countries with high burden of the tuberculosis all over the world and one of 27 countries with high burden of the multi-drug resistant tuberculosis all over the world, whose number of multi-drug resistant tuberculosis patients is the highest one of the whole world; The number of ordinary tuberculosis patients ranks only second to India all over the world.

Although the tuberculosis epidemic in our country presents a serious situation with a large number of infected people, large incident number and large number of current patients, the tuberculosis can be prevented and cured with the modern medical help. In consideration of the fact that the damage of the tuberculosis is serious and the difficulty of the prevention and control work is enormous while the scale of local tuberculosis prevention and control teams at different levels is still small, whose power and expenditure cannot adapt the prevention and control demand, the technology and capital input shall be strengthened and the medical prevention combination mechanism shall be established to form the practical and effective prevention and treatment system. At present, two weak and difficult links of early-stage notice and treatment management exist in the implementation of the prevention and treatment for the tuberculosis. Under such circumstance, the screening program for the tuberculosis patients among the focus groups is gradually launched inside the country by using the essential public health service and free antituberculosis therapy is given for all diagnosed patients.

Being compared with the tuberculosis, the severity degree of damage to the lung cancer on the health of the patients is higher than that of the former. It is commonly acknowledged that the death rate of lung cancer is considerably higher than that of other cancers and it increases by years in recent years. The imageological examination is one of the important technical measures in the aspects of diagnosis, test, prevention and treatment on the cancer. The generally major research object of chest imaging is the lung cancer, which normally observes the corresponding lung images through establishing the lung window. Lung cancer is a neoplastic disease which is related to the smoking, tmospheric pollution and low immunologic function. For example, the repeated inflammatory stimulation of factors like the haze in recent years will bring the chronic damage, affect the normal epithelial function of the bronchial epithelium and the immune antiviral state of the body and have facilitation affect on the occurrence of lung cancer, which may result in the high occurrence of lung cancer in the future. In addition, the carcinogenic incubation period of lung cancer is very long, which normally takes 10 to 30 years. Therefore, some people who ever had tuberculosis when they were young will have the calcification left in their lung after cure and they may mistakenly regard the shadow found in their lung as the calcification due to the tuberculosis in the future medical examination. Consequently, they may miss the chance of early detection of lung cancer.

Being compared with the pulmonary tuberculosis complicating lung cancer, the lung cancer complicating tuberculosis may need more attention. The statistics show that there are about 10%~15% of the lung cancer patients will have tuberculosis incidence and the autopsy cases reach as much as about 30%, which is resulted from the reason that partial lung cancer and tuberculosis are difficult to be distinguished in the imaging and misdiagnose, therapeutic error or delay treatment are extremely easy to happen on clinic. Some patients on clinic only have tuberculosis but they are diagnosed as having lung cancer in several primary hospitals with a imaging examination only. What's the worse, the chemoradiotherapy is conducted for them blindly, which result in serious damage on the body of the patients. On the contrary, some patients do have the lung cancer with complicating tuberculosis but they are diagnosed as the tuberculosis and receive the treatment as that of the pure tuberculosis only. Such phenomenon is mainly resulted from the reason that the clinical manifestations of the tuberculosis and that of the lung cancer are similar, which are cough, hemoptysis and etc. Also, both of them can be shown as the shadow on the chest X-ray radiography through imaging examination.

One large difficult point of the intelligent treatment for the lung DR radiography is the method of confirming the area of the lung lobe. If the scope of lung lobe can be accurately confirmed and the interference outside the lung can be weakened or eliminated, it will be more beneficial for the notice of the slight lesion. In addition, the shape of the lung lobe contour itself also is a important factor for judging relevant physiological index of the people receiving physical examination; Reliable lung lobe contour extraction algorithm can reduce the time of rechecking for the people receiving physical examination and reduce the number of chest images, letting them obtain the definite diagnosis on their nidus from the doctors at the cost of lower radiation dosage.

CONTENTS OF THE INVENTION

This invention aims to solve a technical problem of providing a kind of lung lobe contour extraction method aiming at DR radiography without needing the manual interference, which conducts fully automatic treatment on all kinds of chest X-ray DR radiography and extracts the lung lobe contour.

To solve the technical problem mentioned above, the technical program adopted by this invention is:

A kind of lung lobe contour extraction method aiming at DR radiography, which comprises the steps as follows:

Step 1: Obtain the representative template of the lung lobe contour through offline training, which includes the upper part template of the left lung, lower part template of the left lung, upper part template of the right lung and the lower part template of the right lung;

Step 2: Conduct initialization on the extraction system of contour lobe area in the chest DR radiography and read a DICOM image from the database of DR radiography;

Step 3: In accordance with the dimension of DICOM image, conduct the three-layer pyramid decomposition on the images; Conduct the down sampling process and continuously shrink the DICOM image on the basis of Gaussian smoothing to ½ of the height to the original image and get a series of images, i.e. Gaussian Image Pyramid; Conduct the down sampling process, magnify every image to 2 times of the height to the original image and obtain the difference of the original image under the Gaussian Pyramid, getting the Laplacian image pyramid.

Step 4: Use Gabor filter to rebuild the pending image, convert the residual error of the rebuilt image after Gabor filtering into the black and white image with the self-adaptive local binarization algorithm.

Step 5: Use the Zhan-Suen refinement algorithm to refine the black and white image to get the key contour image which includes other interference in the DICOM image;

Step 6: Call the upper part template of the left lung, lower part template of the left lung, upper part template of the right lung and the lower part template of the right lung of the offline training and take every template as the convolution kernel operator. Conduct convolution on the mentioned contour image in Step 5 and record the calculation result of every convolution;

Step 7: Filter the optimum convolution value with optimum possibility from the convolution result and conduct the combination evaluation;

Step 8: Combine and generate the lung lobe contour shape in accordance with the upper, lower templates of the optimum matching and its optimum matching position.

In accordance with the program mentioned above, the mentioned Step 1 includes the substeps as follows in detail:

Step 1.1: Collect the representative DICOM image as the sample data set;

Step 1.2: Through marking software, manually draw the black and white image corresponding with the sample, in which the white area corresponds with the lung lobe area and the black area corresponds with other areas; Save the black and white image to the file as the contour marks of the sample lung lobe in the data set;

Step 1.3: Conduct traversal on all marked images in the data set, extract the contour in every contour marking image, distinguish the left and right lung contours in accordance with the barycenter of the contour and respectively add the pixels of the left lung contour and right lung contours to the left lung contour point set and the right lung contour point set in accordance with the counter-clockwise order;

Step 1.4: Conduct traversal on the point set of left lung contour, read its corresponding pixel points for the contour of every left lung, judge the maximum value $x_{max}$, $y_{max}$ and minimum value $x_{min}$, $y_{min}$ of coordinate x and y and extract the upper part area and lower part area of the lung lobe in accordance with the $y_{max}$ and $y_{min}$. Therein, the upper part is jointly determined by the parameter $x_{max}$, $x_{min}$ and $y_{min}$ and the lower part is jointly determined by the parameter $x_{max}$, $x_{min}$ and $y_{max}$;

Step 1.5: Use the K-means algorithm to conduct cluster on the upper part contour of the left lung lobe, the lower part contour of the left lung lobe, the upper part contour of the right lung lobe and the lower part contour of the right lung lobe, obtaining the representative template.

In accordance with the program mentioned above, the evaluation indexes of the combination evaluation in the mentioned Step 7 are: matching value of upper part template, matching value of lower part template and the weighted sum of the connectivity matching values of the upper and lower templates.

In accordance with the program mentioned above, the mentioned connectivity matching values of the upper and lower templates are evaluated through the end points of the upper and lower templates and the number of inflection points of three-order Bezier curve constructed by its tangent line.

Being compared with the current existing technology, the beneficial effects of this invention are as follows:

1) This invention makes the subsequent lung disease more targeted through extracting the lung contour, which improves the reliability and accuracy of the computer auxiliary treatment; It can reduce the visual working load of the doctors and improve the overall recognition accuracy and treatment efficiency; And it reduces the influence of the experience difference of the doctors on the judgment for the state of an illness;

2) This invention can adapt all kinds of chest X-ray DR radiography, adapt different figures, and ages of the photographed people and realize the full automatic treatment.

3) This invention can effectively utilize the network resources, realize the function of remote consultation and improves the reliability to the consultation of the difficult and complicated disease.

4) This invention integrates the current medical device and information network resources. It does not need to purchase additional professional devices and its work pattern is totally compatible with the traditional method, making the migration work easy to be accepted. At the same time, it improves the usage rate of the device and prevents the idle device and the resource waste.

SPECIFICATION OF THE ATTACHED FIGURES

SPECIFIC IMPLEMENTATION METHOD

Figure 1:
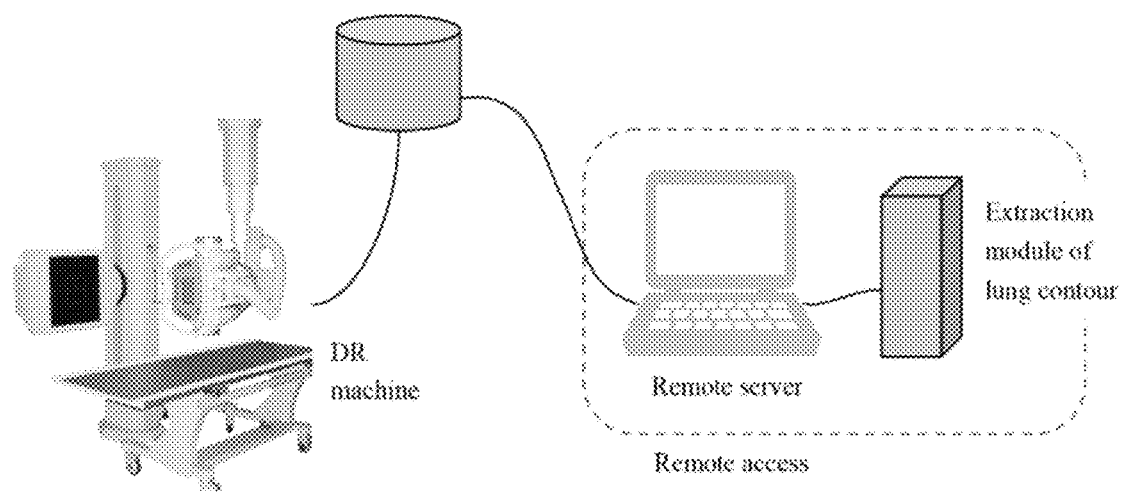
FIG. 1 shows the device connection schematic diagram of this invention.
Figure 2:
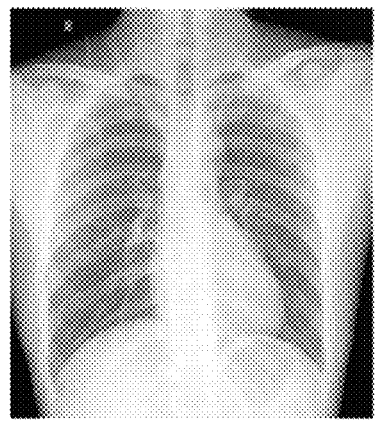
FIG. 2 shows the original contents of DR radiography in this invention.
Figure 3:
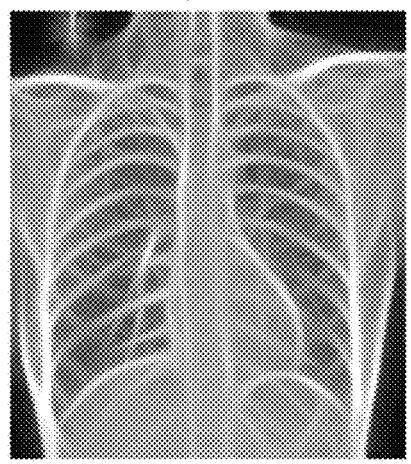
FIG. 3 shows the residual error contents of the DR radiography after Gabor filtering reconstruction in this invention.
Figure 4:
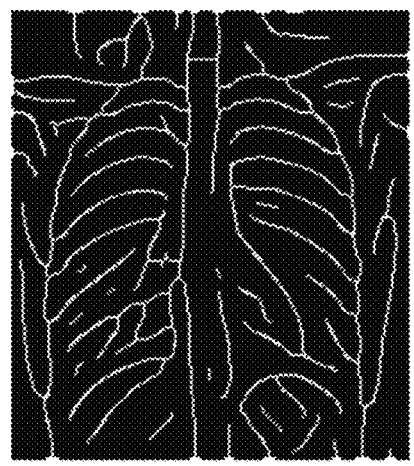
FIG. 4 shows the refining effect of the DR radiography after filtering reconstruction in this invention.
Figure 5:
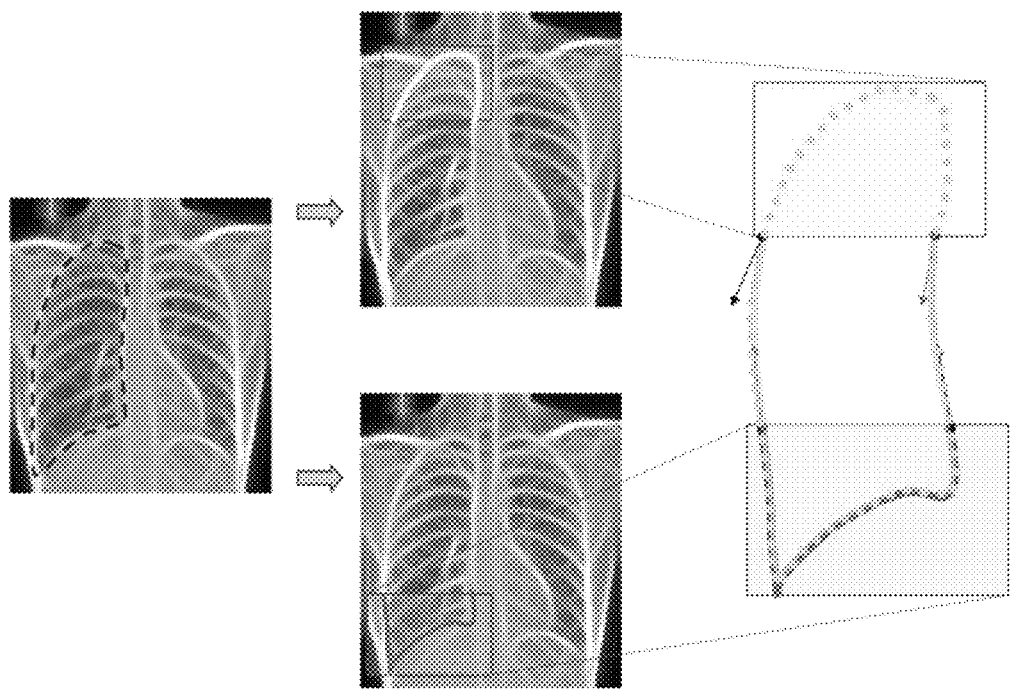
FIG. 5 shows the schematic diagram of automated extraction method for the lung contour of the X-ray DR radiography in this invention.
Figure 6:
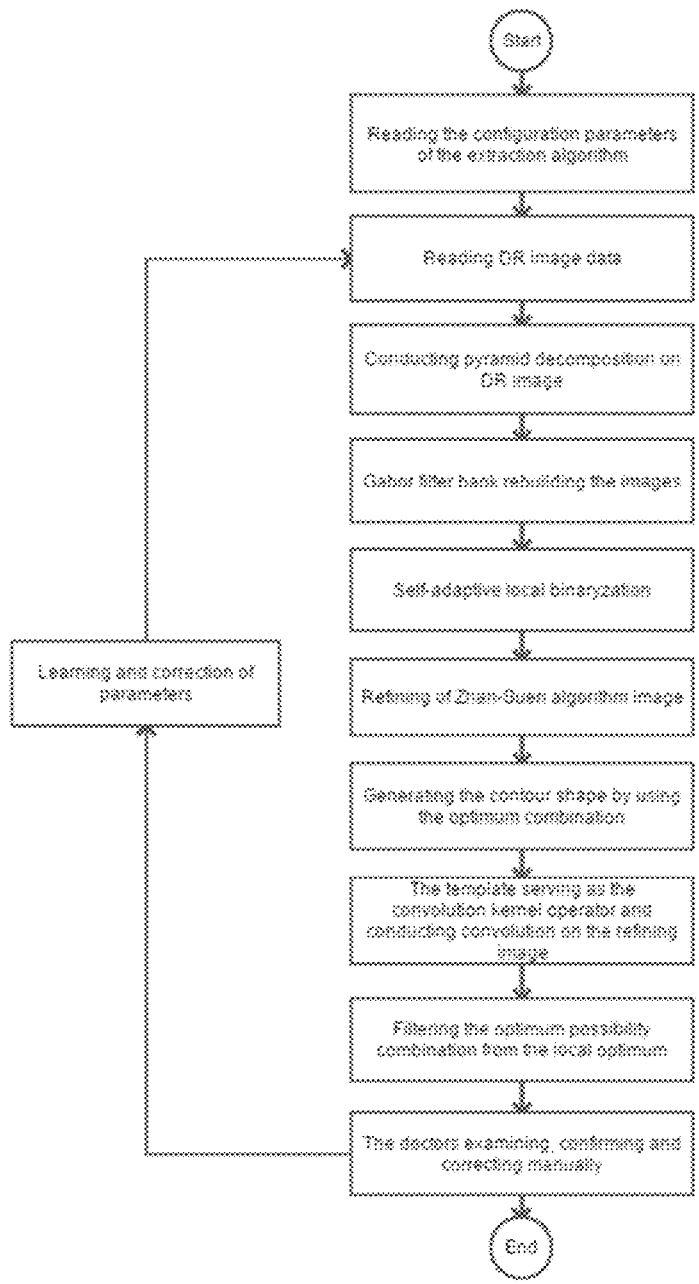
FIG. 6 shows the treatment process schematic diagram of automated extraction method for the lung contour of the chest X-ray DR radiography in this invention.

Further specific specification is given as follows by combining the attached figures and the implementation case in detail. The functions of this invention include: Reading DICOM data of digital chest X-ray imaging (Digital Imaging and Communications in Medicine), using digital imaging treatment technology to detect the lung contour and confirming its area coverage; Making the marked contents become the locally enhanced images which are easy for the doctors to judge the lung nidus shadow, of which the treatment result will be confirmed by the doctors to guarantee the reliability. At the same time, the doctors' feedback information can improve the performance of the system online. The basic thoughts of this invention are: Aiming at the lung rib automated control method of chest X-ray DR radiography and applying it in the basic large-scale medical examination points and the screening of serious infectious diseases, which is mainly composed of the automated treatment functions of the computer. The device spreads the data to the extraction module of lung contour through reading the digital chest X-ray DICOM image data, which comprises the detection steps as follows;

1) The workers in the medical examination points connect the computer which is equipped with DR radiography management module to the DR radiography database and configure the parameters for the reading of DICOM image files.

2) Connect the computers in the medical examination points to the remote medical image data server.

3) After the medical examination is finished, the computers in the medical examination points automatically upload the newly added DR radiography on the same day to the remote server.

4) The system server receives the newly added DR radiography, labels them and add its labels in the pending queue, whose priority of treatment will be determined in accordance with the sequence of time.

5) When the system server scans the data which exists in the pending queue, it will automatically operate the automated extraction module of lung lobe contour and save the extraction results in the files.

6) After the system server conduct batch treatment on a certain quantity of DR images, it will generate the fusion image typed treatment reports of DR original images and the contour extraction results.

7) In accordance with the medical records of the system grade, the system server sends the reports to different doctors, who will confirm the reliability of the segmentation results manually.

8) The doctors use the intelligent terminal devices to open the reports and they can click the confirmation button for the approved lung lobe contour extraction interface; For the unapproved segmentation results, they can choose the manual treatment or delay treatment in accordance with the difficulty degree of the DR images; Therein, the manual treatment normally aims at the intractable cases, for which the program interface of manual marks shall be opened manually to mark the lung lobe area; And the delay treatments is to re-insert the images in the pending queue but reduce its priority of treatment, making the system delay its treatment.

9) At the same time, the system supports the method of crossed evaluation, by which the lung contour with lower reliability of segmentation will be judged by multiple doctors;

10) The system will automatically call the self-adaptive updating module in accordance with the feedback from the doctors to improve the parameters of the current treating modules and conducts the deep process training based on the features of the images newly marked manually by the doctors during the period in which it does not serve for the user terminal devices of the doctors;

11) After the status updating of the system service, it will conduct retreatment on the residual images in the pending lists; Because of the optimizing to the system parameters, the lung field shape in the DR images which can not be treated originally can be extracted correctly in the improved system;

12) After the treatment of a certain batch to the DR radiography in the medical examination points ends, the system server will sends out the message about the ending of the treatment to the computers in the medical examination points and the information staff in the medical examination points will receive and process the results.

In every above step, the system will instruct the doctors for the remote operation in the way of graphical human-computer interaction and then they will automatically recognize and learn dynamically through the computers, which reduces the working frequency of manual intervention needed by the doctors, reduces the workload of the doctors and improves the treatment efficiency while improving the user experience, making the boring marking and verification work easy to be accepted by people; In addition, the system adopts the BS framework, which allows the doctors to conduct marking and evaluation on the tuberculosis images on any computer which is connected to the Internet with user name and password only, making the working platform expand to the wide area universal network rather than the local private network; It is beneficial to both the hospital doctors and the handling of the grass-roots work and the analysis and mining of the data for the local health authorities and disease control and prevention units.

This invention is a method that aims at the chest X-ray image and utilizes the visual technology of the computer to extract the lung contour, which takes the DICOM data as the object of treatment and takes the current existing medical image device, the computer servers and the Internet as the basis. It does no involve the specific designed hardware.

This invention faces the chest X-ray DR radiography image treatment of the medical examination of residents and offers the core algorithms that assist the doctors to launch the screening work for the key lung diseases like tuberculosis. It adopts the computer image treatment technology to automatically obtain the subsequent areas of the possible lung contour boundary in the DICOM images and conducts further filtering to get the optimum matching scheme in the candidate region with high possibility, solving the problem that the data size of the current large-scale residents medical examination is so large that the doctors are very hard to keep the detection with high accuracy due to the manual mark one by one in the limited time.

This invention utilizes the advantage of medical informatization, which can adapt the problems such as the difference resulted from the subjective factors of the medical personnel, device change of the medical examination points, the computer level difference of the operation staff and so on. The whole treating process is easy and convenient, which can fundamentally improve the treating efficiency of the tuberculosis screening while reducing the workload of the medical workers in the medical examination points. Thus, the computer auxiliary screening can be promoted to the grass-root medical organizations which are lack of evaluation experience for the tuberculosis chest X-ray imaging in time, which is more beneficial to the further normalization and standardization of the targeted resident large-scale medical examination on the important infectious disease.

The invention claimed is:

1. A lung lobe contour extraction method used in chest digital radiography, the method comprising the following steps:
    Step 1: obtain a representative template of a lung lobe contour through offline training, the lung lobe contour including an upper part template of a left lung, a lower part template of the left lung, an upper part template of a right lung and a lower part template of the right lung;
    Step 2: conduct initialization on an extraction system of a contour lobe area in the chest digital radiography and read an original Digital Imaging and Communications in Medicine (DICOM) image from a database of the chest digital radiography;
    Step 3: in accordance with a dimension of the original DICOM image, conduct a three-layer pyramid decomposition on the original DICOM image; conduct a down sampling process and continuously shrink the original DICOM image on the basis of Gaussian smoothing to ½ the height of the original DICOM image and generate a series of images, conduct the down sampling process, magnify every image of the series of images to twice the height to the original DICOM image and obtain a difference from the original DICOM image under a Gaussian Pyramid, generating a Laplacian image pyramid;
    Step 4: use a Gabor filter to rebuild a pending image, convert a residual error of the rebuilt pending image after Gabor filtering into a black and white image with a self-adaptive local binarization algorithm;
    Step 5: use a Zhan-Suen refinement algorithm to refine the black and white image to obtain a key contour image which includes interference in the original DICOM image;
    Step 6: use each of the upper part template of the left lung, the lower part template of the left lung, the upper part template of the right lung and the lower part template of the right lung of the offline training as a convolution kernel operator, conduct convolution on the key contour image of Step 5 with respect to each template, and record a calculation result of the convolution with respect to each template;
    Step 7: filter the calculation results to obtain convolution values having a highest possibility of matching; and
    Step 8: combine and generate a lung lobe contour shape in accordance with the upper and lower part templates of the left and right lungs based on the convolution values having the highest possibility of matching.

2. The lung lobe contour extraction method according to claim 1, wherein the Step 1 includes the following sub-steps:
    Step 1.1: collect the original DICOM image as a sample data set;
    Step 1.2: using drawing software, draw a black and white image corresponding with the sample data set, in which a white area corresponds with the contour lobe area and a black area corresponds with other areas not included in the contour lobe area; save the black and white image to a file as contour marks of the lung lobe contour in the sample data set;
    Step 1.3: conduct traversal on all marked images in the sample data set, extract the lung lobe contour in every marked image, distinguish left and right lung contours in accordance with a barycenter of the lung lobe contour and respectively add pixels of the left lung contour and the right lung contour to a left lung contour point set and a right lung contour point set in a counter-clockwise order;
    Step 1.4: conduct traversal on the left lung contour point set, read every left lung contour pixel point for the contour of every left lung, judge a maximum value xmax, ymax and a minimum value xmin, ymin of a coordinate x and y and extract an upper part area and a lower part area of the lung lobe in accordance with the ymax and ymin, therein, the upper part area is jointly determined by the parameters xmax, xmin and ymin and the lower part area is jointly determined by the parameters xmax, xmin and ymax;
    Step 1.5: use a K means algorithm to conduct clustering on an upper part contour of a left lung lobe, a lower part contour of the left lung lobe, an upper part contour of a right lung lobe and a lower part contour of the right lung lobe, obtaining the representative template.

3. The lung lobe contour extraction method according to claim 1, wherein evaluation indexes for the Step 7 are: a matching value of the upper part templates, a matching value of the lower part templates, and a weighted sum of the matching values of the upper and lower part templates.

4. The lung lobe contour extraction method according to claim 3, wherein the matching values of the upper and lower part templates are evaluated through end points of the upper and lower part templates and a number of inflection points of a three-order Bezier curve constructed by a tangent line.

5. The lung lobe contour extraction method according to claim 2, wherein evaluation indexes for the Step 7 are: a matching value of the upper part templates, a matching value of the lower part templates, and a weighted sum of the matching values of the upper and lower part templates.

6. The lung lobe contour extraction method according to claim 5, wherein the matching values of the upper and lower part templates are evaluated through end points of the upper and lower part templates and a number of inflection points of a three-order Bezier curve constructed by a tangent line.

* * * * *